US006825297B1

(12) United States Patent
Devore et al.

(10) Patent No.: US 6,825,297 B1
(45) Date of Patent: Nov. 30, 2004

(54) TRANSITION METAL COMPLEXES AND OLEFIN POLYMERIZATION PROCESS

(75) Inventors: David D. Devore, Midland, MI (US); Kevin A. Frazier, Midland, MI (US); Shaoguang S. Feng, Midland, MI (US); Jasson T. Patton, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/958,446

(22) PCT Filed: Mar. 17, 2000

(86) PCT No.: PCT/US00/07164

§ 371 (c)(1),
(2), (4) Date: Oct. 5, 2001

(87) PCT Pub. No.: WO00/69923

PCT Pub. Date: Nov. 23, 2000

Related U.S. Application Data

(60) Provisional application No. 60/134,336, filed on May 14, 1999.

(51) Int. Cl.$^7$ ............ B01J 31/00; B01J 37/00; C08F 4/60; C08F 10/00
(52) U.S. Cl. ............ 526/172; 526/145; 526/146; 526/147; 526/351; 526/348.6; 526/352; 502/162; 502/155; 502/152
(58) Field of Search ............ 502/103, 104, 502/118, 150, 152, 208, 200, 216, 162, 247, 258, 238, 155; 526/72, 92, 89, 145, 146, 147, 351, 172, 348.6, 352

(56) References Cited

U.S. PATENT DOCUMENTS 6,242,377 B1 * 6/2001 Hirahata et al. ............ 502/117
6,281,303 B1 * 8/2001 Lavoie et al. ............ 526/127

FOREIGN PATENT DOCUMENTS

| WO | WO 98/27124 | 6/1998 |
| WO | WO 98/30612 | 7/1998 |
| WO | WO 99/02472 | 1/1999 |
| WO | WO 99/12981 | 3/1999 |

OTHER PUBLICATIONS

Chemical Abstracts, vol. 47, No. 4, (1971) Abstract # 18852, Baci, M. et al "Oxomolybdenum(IV) and Oxovanadium(IV) Complexes with a Tridentate Schiff Base", (xp 002141499), no month.

Chemical Abstracts, vol. 117, No. 6, (1992), Abstract # 61528, Ruettimann, Stephane et al., "Complexes of Structural Analogs of Terpyridyl with iron and Zinc; the x–ray crystal structure of Bis[2, 6–Bis(Benzimidazol–2–yl)Pyridine]Iron(II) Trifluoromethylsulfonate Bis–Ethanol Solvate" (XP002141501), no month.

J. Am. Chem. Soc. 1999, 121, 9318–9325, D. Reardon, F. Conan, S. Gambarotta, G. Yap, and Q. Wang Life and Death of an Active Ethylene Polymerization Catalyst. Ligand Involvement in Catalyst Activation and Deactivation. Isolation and Characterization of Two Unprecedented Neutral and Anionic Vanadium(I) Alkyls, no month.

Chemical Abstracts, vol. 114, No. 14, (1991) Abstract # 134883, Edwards, Dennis A. et al, "Manganese (II) Complexes Containing the Tridentate Ligands 2,6–Bis [1–4–Methoxyphenylimino)Ethyl]Pyridine, L2. The Molecular Structure of Five–Co–Ordinate[MnBr2L1] and The Zinc Analogue [ZNCL2L1]" 9XP002141500), no month.

Macromolecules : Rapid Communications, vol. 19, No. 12, (1988), pp. 651–655,C. Pellecchia et al, "Isotactic–Specific Polymerization of Propene With An Iron–Based Catalyst: Polymer and Groups And Regiochemistry of Propagation" (XP000803762), no month.

Chemical Communications, GB, Royal Society of Chemistry, No. 7, (1998) pp. 849–850, Birtovsek et al, "Novel Olefin Polymerization Catalysts Based on Iron and Cobalt" (XP002086893), no month.

Chemical Abstracts, vol. 128, No. 12, (1998), Yasuhiko et al, "Selective Preparation of .Alpha.—Olefin Oligomers Especialy for Forming 1–Hexene from Ethylene" (XP002141498), no month.

Macromolecules, US American Chemical Society, vol. 32 No. 7, (1999), pp. 2120–2130, B.L. Small et al., "Polymerization of propylene by a New Generation of Iron Catalysts: Mechanisms of Chain Initiation. Propagation, and Termination" (XP000828310), no month.

The Journal of the American Chemical Society, US, American Chemical Society, vol. 120, No. 16, (1998), pp. 4049–4050, B.L. Small et al, "Highly Active Iron and Cobalt Catalysts for the Polymerization of Ethylene" (XP002119954), no month.

* cited by examiner

*Primary Examiner*—Michael La Villa

(57) ABSTRACT

Metal complexes comprising a polydentate chelating group, catalysts and polymerization processes using the same for the polymerization of olefins, especially propylene, are disclosed.

7 Claims, No Drawings

TRANSITION METAL COMPLEXES AND OLEFIN POLYMERIZATION PROCESS

CROSS-REFERENCE TO RELATED APPLICATION

This application claims benefit under 35 USC § 119 of provisional application No. 60/134,336 filed on May 14, 1999.

FIELD OF THE INVENTION

This invention relates to a class of metal complexes, the ligands used to prepare these metal complexes and to olefin polymerization catalysts derived therefrom that are particularly suitable for use in a polymerization process for preparing polymers by polymerization of α-olefins and mixtures of α-olefins. Additionally, the present invention relates to an improved olefin polymerization process useful for preparing polymers of prochiral olefins having a high degree of isotacticity and low polymer chain defect content. Such polymers possess a correspondingly high crystalline melting point

BACKGROUND

Metal complexes containing polydentate chelating ligands are well known in the art. Examples include complexes based on acetylacetonate (AcAc), tetramethylethylenediamine, and other polydentate chelating ligands. While such complexes with transition metals are well known in the art, seldom are such metal complexes useful as catalyst components for addition polymerizations, especially olefin polymerizations. Examples of previously known work in this field are found in WO 98/030612, *Chem. Commun.*, 1998, 849, *JACS*, 1998, 120, 4049, and elsewhere.

Despite advances in the present art, there remains a need for metal complexes having improved catalytic properties. It would be advantageous to be able to produce polyolefins with improved physical properties. It would also be especially advantageous to be able to produce crystalline polyolefins, particularly crystalline, isotactic polypropylene or poly(2-butene) using polymerization catalyst compositions that give polymers of high crystallinity and few chain defects. Such polymers possess extremely high strength properties, particularly at high use temperatures.

SUMMARY OF THE INVENTION

According to the present invention there are provided metal complexes comprising a multidentate chelating ligand, said metal complexes corresponding to the formula:

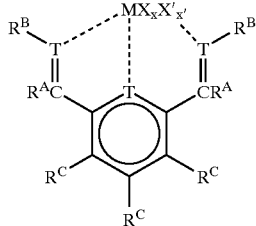

I where M is a metal from one of Groups 3 to 13 of the Periodic Table of the Elements, the lanthanides or actinides;

T is nitrogen or phosphorus;

$R^A$ independently each occurrence is hydrogen, $R^B$ or T $R^B_j$;

$R^B$ independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, and optionally the $R^B$ and $R^A$ groups bonded to the same T=C grouping may be joined together to form a divalent ligand group;

j is is 1 or 2, and when j is 1, T' is oxygen or sulfur and when j is 2, T' is nitrogen or phosphorus, $R^C$ independently each occurrence is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino substituted hydrocarbyl, or hydrocarbylsilyl- substituted hydrocarbyl, or two $R^C$ groups are joined together forming a divalent ligand group;

X is an anionic ligand group having up to 60 atoms (excluding ligands that are cyclic, delocalized, π-bound ligand groups), and optionally two X groups together form a divalent ligand group;

X' independently each occurrence is a Lewis base ligand having up to 20 atoms;

x is a number from 0 to 5; and x' is zero, 1 or 2.

Also, according to the present invention, there is provided a catalyst composition for olefin polymerization comprising:

(A) a catalyst component comprising the foregoing metal complex; and (B) a cocatalyst component comprising an activating cocatalyst wherein the molar ratio of (A) to (B) is from 1:10,000 to 100:1.

Further according to the present invention there is provided a process for the polymerization of olefins comprising contacting one or more $C_{2-20}$ α-olefins under polymerization conditions with one of the aforementioned catalyst compositions. A preferred process of this invention is a high temperature solution polymerization process for the polymerization of prochiral olefins comprising contacting one or more $C_{3-20}$ α-olefins under polymerization conditions with one of the aforementioned catalyst compositions at a temperature from 30 to 250° C., more preferably from 50 to 220° C., most preferably from 70 to 200° C.

In a further embodiment of the invention, there is provided a polymerization process for preparing isotactic polypropylene having an isotacticity as measured by $^{13}C$ NMR triads of greater than 75 percent, preferably greater than 85 percent, more preferably greater than 95 percent comprising contacting propylene at a temperature from 50 to 220° C., preferably from 70 to 200° C. under polymerization conditions with the foregoing catalyst composition.

Preferably, the metal, M, is a metal of Group 3 or 5–8 of the Periodic Table of the Elements.

Within the scope of this invention are the polyolefin and polypropylene products produced by the aforementioned processes. Preferred products have a high degree of crystallinity and relatively few polymer chain defects.

This invention also provides a multi-dentate chelating ligand corresponding to the formula:

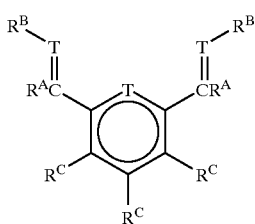

II where the ligand is in the form of a free base capable of being deprotonated, a Group 1 or 2 metal salt, or a Group 2 metal halide salt.

Within the scope of this aspect of the invention is the use of one of these ligands of formula II for synthesis to produce a metal complex of formula I of this invention, or, more specifically, the use of one of these ligands of formula II for synthesis to produce a metal complex comprising a metal from one of Groups 3 to 13 of the Periodic Table of the Elements, the lanthamides or actinides, and at least 1 of the foregoing ligands of formula II.

The present catalysts and processes may be used in the solution or bulk polymerization, slurry polymerization or gas phase polymerization of ethylene/propylene (EP polymers), ethylene/octene (EO polymers), ethylene/styrene (ES polymers), propylene homopolymers, copolymers of propylene with ethylene and/or $C_{4-10}$ α-olefins, and ethylenepropyleneldiene (EPDM copolymers) wherein the diene is ethylidenenorbornene, 1,4-hexadiene or similar nonconjugated diene. As previously slated, the catalysts are especially desirable for use in the polymerization of propylene to give isotactic polypropylene of high isotacticity.

The catalysts of this invention may also be supported on a support material and used in olefin polymerizatuon processes. The catalyst may also be prepolymerized with one or more olefin monomers in situ in a polymerization reactor or in a separate process with intermediate recovery of the prepolymerized catalyst prior to the primary polymerization process. Highly desirably, the catalyst compositions of the present invention produce highly isotactic polymers of prochiral α-olefins, especially, propylene, having tacticity (as measured by repeat mm diadds in the $^{13}C$ NMR spectrum) of greater than 95 percent, preferably greater than 96 percent. Further uniquely, the present invented polymerization process attains such highly isotactic polymers at polymerization temperatures greater than 70° C., preferably greater than 90° C. and the polymer has very low chain defects, preferably less than 0.1 mole percent, more preferably less than 0.01 mole percent. Such polymers are highly crystalline and have high crystalline mering points due to the uniform nature of the polymer chains.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups. The full teachings of any patent, patent application, provisional application, or publication referred to herein are hereby incorporated by reference. The term "comprisingr when used herein with respect to a composition or mixture is not intended to exclude the additional presence of any other compound or component.

Olefins as used herein are $C_{2-20}$ aliphatic or aromatic compounds containing vinylic unsaturation, as well as cyclic compounds such as cyclobutene, cyclopentene, and norbornene, including norbornene substituted in the 5- and 6-positions with $C_{1-20}$ hydrocarbyl groups. Also included are mixtures of such olefins as well as mixtures of such olefins with $C_{4-20}$ diolefin compounds. Examples of the latter compounds include ethylidene norbornene, 1,4-hexadiene, norbornadiene, and the like. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylenE/1 octene copolymers as well as terpolymers of ethylene, propylene and a nonconjugated diene, such as, for example, EPDM terpolymers.

Illustrative $T'R^B_i$ groups include methoxy, ethoxy, propoxy, methylethyloxy, 1,1-dimethyethyloxy, trimethylsiloxy, 1,1-dimethylethyl(dimethylsilyl)oxy, dimethylamino, diethylamino, methylethylamino, methylphenylamino, dipropylamino, dibutylamino, piperidino, morpholino, pyrrolidino, hexahydro-1H-azepin-1-yl, hexahydro-1 (2H)-azocinyl, octahydro-1H-azonin-1-yl or octahydro-1 (2H)-azecinyl, or two adjacent $TR^B_j$ groups are —$OCH_2O$—. More preferred are those wherein the $R^B_jT'$ group is dimethylamino, methylphenylamino, piperidino or pyrrolidino.

Preferred X groups are halide, hydrocarbyl (including alkyl, alkenyl, aryl, alkaryl, aralkyl cycloalkyl and cycloalkenyl) hydrocarbyloxide, hydrocarbylsulfide, N,N-dihydrocarbylamide, hydrocarbyleneamide, hydrocarbylcarboxylate, acetylacetonate, cyano, dithiocarbamate, and dithiocarboxylate groups, said X having from 1 to 20 atoms other than hydrogen.

Preferred X' groups are carbon monoxide; phosphines, especially trimethylphosphine, triethylphosphine, triphenylphosphine and bis(1,2-dimethylphosphino)ethane; $P(OR^j)_3$, wherein $R^j$ is hydrocarbyl, silyl or a combination thereof; ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including the latter X' groups include those wherein the metal is in the +2 formal oxidation state.

More preferred $R^A$ groups are hydrogen, alkyl, aryl, aralkyl, alkoxy, dihydrocarbylamino, and hydrocarbyleneamino, said R group having from 1 to 20 nonhydrogen atoms, most preferably hydrogen, alkyl, aryl, N,N-dimethylamino and pyrrolidino.

Preferred coordination complexes according to the present invention are complexes corresponding to the formula I:

where M is a metal of Groups 4–8; preferably titanium, vanadium, iron or chromium;

T is nitrogen;

X is chloride or $C_{1-10}$ hydrocarbyl; and x' is zero.

More preferably independently each occurrence $R^A$ is hydrogen, methyl or phenyl, $R^B$ is aryl or alkyl substituted aryl, and $R^C$ is hydrogen.

Most highly preferred complexes correspond to the formula:

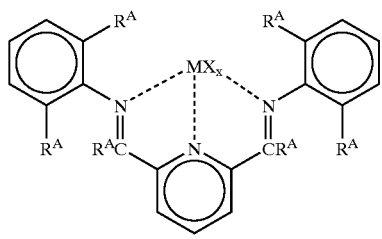

III wherein $R^A$ independently each occurrence is $C_{1-4}$ alkyl, most preferably methyl or isopropyl.

Formation of the polydentate chelating ligands and ultimately the metal complexes themselves uses conventional organic- and organometallic- synthetic procedures. The reactions are conducted in a suitable noninterfering solvent at a temperature from −100 to 300° C., preferably from −78 to 100° C., most preferably from 0 to 50° C.

Suitable reaction media for the formation of the polydentate chelating ligands and complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The complexes and compounds are rendered catalytically active by combination with an activating cocatalyst. Suitable activating cocatalysts for use herein include polymeric or oligomeric alumoxanes, mixtures of such alumoxanes with one or more $C_{1-20}$ hydrocarbyl substituted Group 13 metal Lewis acid compounds, and mixtures of such alumoxanes or alumoxane/Lewis acid mixtures with one or more aliphatic or aromatic ethers. Preferred Lewis acids especially include tri(hydrocarbyl)aluminum- or tri(hydrocarbyl)boron- compounds and halogenated (including perhalogenated) derivatives thereof, having from 1 to 15 carbons in each hydrocarbyl or halogenated hydrocarbyl group, more especially pernluorinated tri(aryl)boron compounds, and most especially tris(o-nonafluorobiphenyl)borane, tris(pentafluorophenyl)borane; tris(o-nonafluorobiphenyl)aluminum; tris(pentafluorophenyl)aluminum, and mixtures thereof. Preferred ethers include diethyl ether and diisopropyl ether.

Suitable polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butane, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1, 1-hexene, 1-octene, and combinations of ethylene and/or propene with one or more of such other alpha-olefins. Other preferred monomers include styrene, halo- or alkyl substituted styrenes, tetrafluoroethylene, vinylchloride, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for solution phase, slurry, gas phase and high pressure Ziegler-Natta or Kaminsky-Sinn type polymerization reactions. Examples of such well known polymerization processes are depicted in U.S. Pat. No. 5,084,534, U.S. Pat. No. 5,405,922, U.S. Pat. No. 4,588,790, U.S. Pat. No. 5,032,652, U.S. Pat. No. 4,543,399, U.S. Pat. No. 4,564,647, U.S. Pat. No. 4,522,987, and elsewhere. Preferred polymerization pressures are from atmospheric to 3000 atmospheres. Molecular weight control agents can be used in combination with the present cocatalysts. Examples of such molecular weight control agents include hydrogen, silanes or other known chain transfer agents. The catalyst composition may be used by itself (homogeneously) or supported on a support material. Suitable support materials include metal halides, metal oxides, metal nitrides, metalloid oxides, metalloid carbides, clays and polymeric hydrocarbons. Preferred supports include silica, alumina, aluminosilicates, clays, borosilicates, boron nitrides, boron carbides, mixed oxides of magnesium and aluminum and/or silicon, including expanded clay materials, and the foregoing materials having residual hydroxyl groups thereof reacted with trialkyl aluminum compounds.

The catalyst composition (whether based on a catalyst complex or catalyst compound) may further comprise an electron donor compound which may interact with either the metal complex or metal compound, the support, or the combination of the metal complex and support or metal compound and support to give improved (greater quantity) of isospecific polymer formation. Suitable electron donors include both internal donor and external donors. Specific examples include alkyl esters- or alkyl diesters- of aromatic acids, especially $C_{1-4}$ alkylbenzoates, most especially ethylbenzoate, or $C_{1-4}$ dlalkylphthalates, most especially dibutyl phthalate; and alkylsiloxanes, especially phenyl triethyloxysilane. Electron donors are previously known in the art for improved isoselective polymer formation, and have been discussed in K. Soga, et at., *Prog. Polym. Sci.* 22, 1503–1546, (1997), and elsewhere.

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. Where stated, the term "room temperature" refers to a temperature from 20 to 25° C., the term "overnight" refers to a time from 12 to 18 hours, and the term "mixed alkanes" refers to a mixture of propylene oligomers sold by Exxon Chemicals Inc. under the trade designation Isopar™ E.

$^1$H (300 MHz) and $^{13}$C NMR (75 MHz) spectra were recorded on a Varian XL-300 spectrometer. $^1$H and $^{13}$C NMR spectra are referenced to the residual solvent peaks and are reported in ppm relative to tetramethylsilane. All J values are given in Hz. Tetrahydrofuran (THF), diethylether, toluene, and hexane were used following passage through double columns charged with activated alumina and catalyst (Q-5®, available from Englehardt Chemicals Inc.). All reagents were purchased or prepared according to published techniques. All syntheses were performed under dry nitrogen or argon atmospheres using a combination of glove box and high vacuum techniques at room temperature unless indicated otherwise.

Examples 1–3

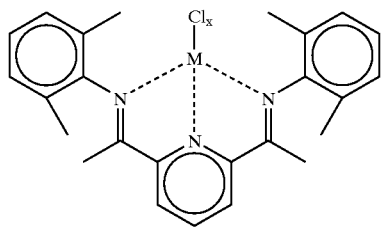

1. Preparation of: [2,6-Bis[1-[2,6(dimethylphenyl)imino]ethyl)pyridine]CrCl$_2$

1A. Preparation of 2,6-Bis(1-[2,6(dimethylphenyl)imino]ethyl)pyridine 2,6-Diacetylpyridine (5.360 g, 32.85 mmol), 2,6-dimethylaniline (7.961 g, 65.70 mmol), and p-toluenesulfonic acid (0.01 g) were refluxed together in toluene (150 mL) during which time water was removed from the reaction mixture using a Dean-Stark apparatus. The reaction was allowed to proceed overnight. The reaction mixture was then allowed to cool to room temperature and filtered. Removal of the volatiles under vacuum resulted in the isolation of a yellow powder. This powder was then washed well with hexane and dried under vacuum resulting in the isolation of the desired product as a pale yellow powder (10.1 g, 83.1 percent yield).

$^1$H NMR (C$_5$D$_6$): δ 2.05 (s, 12 H), 2.17 (s, 6 H), 6.9–7.1 (m, 6 H), 7.29 (t, $^3J_{HH}$=7.7 Hz, 1H), 8.50 (d, $^3J_{HH}$=7.9 Hz, 2 H). $^{13}$C NMR(C$_6$D$_6$): δ 16.46, 18.25, 122.51, 123.43, 125.38, 136.86, 149.43, 155.48, 166.78.

1B. Preparation of [2,6-Bis(1-[2,6(dimethylphenyl)imino]ethyl)pyridine]CrCl$_2$ 2,6-Bis(1-[2,6(dimethylphenyl)imino]ethyl)pyridine (0.500 g, 1.26 mmol) and CrCl$_2$ (0.155 g, 1.26 mmol) were mixed together and stirred in THF (75 mL) overnight during which time a dark purple solution formed. The volatiles were then removed under vacuum and the residue extracted and filtered using CH$_2$Cl$_2$. Removal of the CH$_2$Cl$_2$ resulted in the isolation of a dark purple microcrystalline solid (0.427 g, 68.8 percent yield).

2. Preparation of [2,6-Bis(1-[2,6(dimethylphenyl)imino]ethyl)pyridine]FeCl$_3$ 2,6-Bis(1-[2,6(dimethylphenyl)imino]ethyl)pyridine (0.251 g, 0.68 mmole) and FeCl$_3$ (0.100 g, 0.62 mmole) were dissolved in 30 mL of THF. The slurry was stirred for 20 hours resulting in the formation of a yellow solid. The product was isolated by filtration, washing with Et$_2$O, and drying under vacuum. Yield was 0.30 g, 91.5 percent.

3. Preparation of 12,6-Bis(1-[2,6(dimethylphenyl)imino]ethyl)pyridine]VCl$_3$ 2,6-Bis(1-[2,6(dimethylphenyl)imino]ethyl)pyridine (0.109 g, 0.29 mmole) and VCl$_3$(3THF) (0.100 g, 0.27 mmole) were dissolved in 20 mL of THF. The slurry was stirred for 20 hours resulting in the formation of a purple solid. The product was isolated by filtration, washing with Et$_2$O, and drying under vacuum. Yield was 0.120 g, 85.1 percent.

4. Preparation of [2,6-Bis(1-[2,(dimethylphenyl)imino]ethyl)pyridine]TiCl$_3$ 2,6-Bis(1-[2,6(dimethylphenyl)imino]ethyl)pyridine (0.309 g, 0.89 mmole) and TiCl$_3$(3THF) (0.300 g, 0.81 mmole) were dissolved in 40 mL of THF. The slurry was stirred for 20 hours resulting in the formation of a purple solid. The product was isolated by filtration, washing with Et$_2$O, and drying under vacuum. Yield was 0.38 g, 89.4 percent.

Examples 5–9

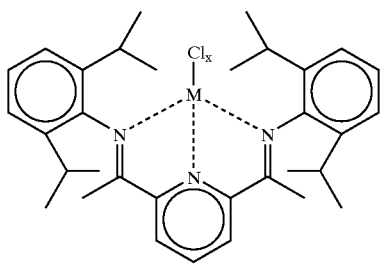

5. Preparation of 2,6-Bis(1-[2,6(diisopropylphenyl)imino]ethyl)pyridine]CrCl$_2$ 5A. Preparation of 2,6-Bis(1-[2,6(diisopropylphenyl)imino]ethyl)pyridine 2,6-Diacetylpyridine (4.000 g, 24.51 mmol), 2,6-diisopropylaniline (9.561 g, 53.93 mmol), and p-toluenesulfonic acid (0.01 g) were refluxed together in toluene (100 mL) during which time water was removed from the reaction mixture using a Dean-Stark apparatus. The reaction was allowed to proceed overnight during which time a yellow precipitate formed. The reaction mixture was then allowed to cool to room temperature and the yellow solid isolated via filtration. The solid was then washed through the frit using CH$_2$Cl$_2$. The solution was then concentrated and cooled and the solid recovered by filtration and dried under vacuum resulting in the isolation of the desired product as a pale yellow solid. Yield was 10.004 g, 84.7 percent).

$^1$H NMR (C$_6$D6): δ 1.16 (d, $^3J_{HH}$=6.6 Hz, 6 H), 1.20 (d, $^3J_{HH}$=6.6 Hz, 6H), 2.28 (s, 6 H), 2.92 (septet, $^3J_{HH}$=6.6 Hz, 4 H), 7.1–7.4 (m, 7 H), 8.50 (d, $^3J_{HH}$=7.7 Hz, 2 H). $^{13}$C NMR (C$_6$D$_6$): δ 17.23, 23.06, 23.59, 28.96, 122.51, 123.53, 124.31, 147.10, 155.62, 166.92.

5B. Preparation of [2,6-Bis(1-[2,6(diisopropylphenyl)imino]ethyl)pyridine]CrCl$_2$ 2,6-Bis(1-[2,6(diisopropylphenyl)imino]ethyl)pyridine (1.000 g, 2.08 mmol) and CrCl$_2$ (0.329 g, 2.08 mmol) were mixed together and stirred in THF (100 mL) for three hours during which time the mixture became intensely purple. The mixture was then refluxed for one hour, cooled to room temperature, and the volatiles removed under vacuum. The residue was then redissolved in CH$_2$Cl$_2$ and filtered. Removal of the CH$_2$Cl$_2$ resulted in the isolation of a deep purple microcrystalline solid. Yield was 1.09 g, 86.8 percent.

6. Preparation of [2,6-Bis(1-[2,6(diisopropylphenyl)imino]ethyl)pyridine]Cr(CH$_2$TMS)$_2$ 2,6-Bis(1-[2,6(diisopropylphenyl)imino]ethyl)pyridine]CrCl$_2$ (0.180 g, 0.300 mmol) was stirred in diethylether (50 mL) at 0° C. as LiCH$_2$TMS (0.60 mmol, 0.60 mL of 1.0 M solution in diethylether) was added dropwise. This mixture was then allowed to stir overnight at room temperature during which time the solution turned from deep purple to green. After the reaction period the volatiles were removed and the residue extracted and filtered using hexane. Concentration of the hexane and cooling to −10° C. overnight resulted in the precipitation of dark green crystals (0.063 g, 31.1 percent yield).

7. Preparation of [2,6-Bis(1-[2,6(diisopropylphenyl)imino]ethyl)pyridine)MnCl$_2$ 2,6-Bis(1-[2,6(diisopropylphenyl)imino]ethyl)pyridine (0.500 g, 1.04 mmol) and MnCl$_2$ (0.131 g, 1.04 mmol) were mixed together and stirred in THF (75 mL) overnight. The volatiles were then removed under vacuum and the residue extracted and filtered using CH$_2$Cl$_2$. Removal of the CH$_2$Cl$_2$ resulted in the isolation of a yellow microcrystalline solid (0.519 g, 82.2 percent yield).

8. Preparation of [2,6-Bis(1-[2,6(diisopropylphenyl)imino]ethyl)pyridine]FeMe$_2$

[2,6Bis(1-[2,6(diisopropylphenyl)imino]ethyl)pyridine]FeCl$_2$ (0.60 g, 0.99 mmol, prepared according to published procedures) was stirred in Et$_2$O (30 mL) at −20° C. as MgMeBr (2.0 mmol, 2.0 mL of 1.0 M solution in diethylether) was added dropwise. This mixture was then allowed to stir for two hours at room temperature to give a brown solution. After the reaction period the solvent was removed and the residue extracted and filtered with hexane. The concentrated hexane solution was cooled to −20° C. overnight resulted in the precipitation of dark brown solids (0.15 g, 26.7 percent).

9. Preparation of [2,6-Bis(1-[2,6(diisopropylphenyl)imino)ethyl)pyridine]FeMe$_2$

[2,6-Bis(1-[2,6(diisopropylphenyl)imino]ethyl)pyridine)FeCl$_2$ (0.60 g, 0.99 mmol, prepared according to published procedures) was stirred in hexanes (30 mL) at −20° C. as excess AlEt$_3$ (4.0 mmol, 4.0 mL of 1.0 M solution in heptane) was added slowly. This mixture was then allowed to stir for five hours at room temperature to give a brown solution. After the reaction period the solvent was removed and the residue extracted and filtered with hexane. The concentrated hexane solution was cooled to −20° C. overnight resulted in the precipitation of dark brown solids (0.17 g, 29 percent).

Examples 10–11

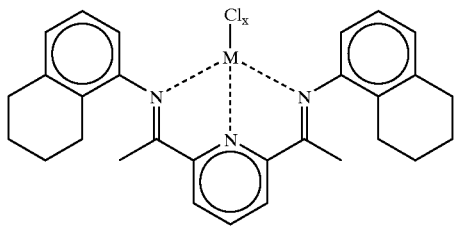

10. Preparation of [2,6Bis(1-[1-amino-5,6,7,8-tetrahydronapthalene)imino)ethyl]pyridine]CrCl$_2$ 10A. Preparation of [2,6-Bis(1-[1-amino-5,6,7,8-tetrahydronapthalene)imino]-ethyl)pyridine]

2,6-Diacetylpyridine (5.54 g, 33.96 mmol), excess 5,6,7,8,tetrahydro-1-naphthylamine (11.00 g, 74.72 mmol), and p-toluenesulfonic acid (0.10 g) were dissolved in 150 mL of toluene. The mixture was refluxed for ten hours using a Dean-Stark apparatus to remove water from the reaction mixture. The solvent was then removed and the solid was flurried with 1:1 of H$_2$O:iso-PrOH. The solid was then isolated by filtration and washed with H$_2$O, i-PrOH, and Et$_2$O. The product was dried under vacuum to give a yellow solid (12.5 g, 87.0 percent yield).

$^1$H NMR (CD$_2$Cl$_2$, ppm): δ 1.83 (m, 8 H), 2.38 (s, 6 H), 2.48 (broad, 4 H), 2.86 (broad, 4H), 6.53 (d, $^3J_{HH}$A=7.5 Hz, 2H), 6.90 (d, 3=7.5 Hz, 2H), 7.15 (t, $^3J_{HH}$=7.5 Hz, 2H), 7.93 (t, $^3J_{HH}$=8.1 Hz, 1H), 8.45 (d, $^3J_{HH}$=8.1 Hz, 2H). $^{13}$C NMR (CD2Cl$_2$): δ 16.37, 23.44, 23.54, 25.54, 30.19, 115.22, 122.37,124.66, 125.87, 126.95, 137.04, 138.48,150.14, 155.84, 166.65.

10B. Preparation of [2,6-Bis(1-[1-amino-5,6,7,8-tetrahydronapthalene)imino]-ethyl)pyridine]CrCl$_2$ 2,6-Bis(1-[1-imino-5,6,7,8-tetrahydronaphthalene)imino]ethyl} pyridine (0.500 g, 1.19 mmol) and CrCl$_2$ (0.46 g, 1.19 mmol) were mixed together and stirred in THF (75 mL) overnight during which time a dark green solution formed. The volatiles were then removed under vacuum and the residue extracted and filtered using CH$_2$Cl$_2$. Removal of the CH$_2$Cl$_2$ resulted in the isolation of a dark green microcrystalline solid (0.514 g, 71.5 percent yield).

11. Preparation of [2,6-Bis(1-[1-amino-5,6,7,8-tetrahydronapthalene)imino]-ethyl)pyridine]FeCl$_2$ 2,6-Bis(1-[1-amino-5,6,7,8-tetrahydronapthalene)imino]ethyl)pyridine (1.10 g, 2.60 mmole) and FeCl$_2$ (0.300 g, 2.37 mmole) were dissolved in 50 mL of THF. The slurry was stirred for 20 resulting in the formation of blue solids. The microcrystalline product was isolated by filtration, washing with Et$_2$O, and drying under vacuum (1.13 g, 87.0 percent).

Examples 12–18

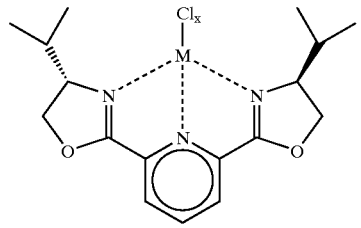

12. Preparation of [2,6-Bis-(4S-isopropyl-2-oxazlin-2-yl)pyridine]MnCl$_2$ 2,6-Bis-(4S-isopropyl-2-oxazlin-2-yl)pyridine (0.400 g, 1.33 mmol) and MnCl$_2$ (0.167 g, 1.33 mmol) were mixed together and stirred in THF (75 mL) overnight during which lime a yellow solution formed. The volatiles were then removed under vacuum and the residue extracted and filtered using CH$_2$Cl$_2$. Concentration of the solution and cooling to −10° C. overnight resulted in the isolation of a yellow microcrystalline solid (0.301 g, 53.1 percent yield).

13. Preparation of [2,6-Bis-(4S-isopropyl-2-oxazlin-2-yl)pyridine]CrCl$_2$

[2,6-Bis-(4S-isopropyl-2-oxazlin-2-yl)pyridine] (0.400 g, 1.33 mmol) and CrCl$_2$ (0.163 g, 1.33 mmol) were mixed together and stirred in THF (75 mL) overnight during which time a deep purple solution formed. The volatiles were then removed under vacuum and the residue extracted and filtered using CH$_2$Cl$_2$. Removal of the CH$_2$Cl$_2$ under vacuum resulted in the isolation of a purple microcrystalline solid (0.539 g, 95.8 percent yield).

14. Preparation of [2,6-Bis(4S-isopropyl-2-oxazlin-2-yl)pyridine]FeCl$_2$

[2,6-Bis-(4S-isopropyl-2-oxazlin-2-yl)pyridine] (0.523 g, 1.74 mmole) and FeCl$_2$ (0.200 g. 1.58 mmole) were dissolved in 30 mL of dry THF and the mixture was then stirred for 15 hours until no detectable FeCl$_2$ left. The solvent was reduced to ca. 10 mL. The resulting blue crystalline solid was then filtered, washed with hexane, and dried under vacuum to give the desired product (0.630 g, 91.7 percent yield).

15. Preparation of [2,6-Bis-(4S-isopropyl-2-oxazlin-2-yl)pyridine]FeCl$_3$

[2,6-Bis-(4S-isopropyl-2-oxazlin-2-yl)pyridine] (0.204 g, 0.68 mmole) and FeCl$_3$ (0.100 g, 0.62 mmole) were dissolved in 30 mL of THF. The slurry was stirred for 20 hours resulting in the formation of a yellow solid. The product was isolated by filtration, washing with Et$_2$O, and drying under vacuum (0.240 g, 83.4 percent yield).

16. Preparation of [2,6-Bis-(4S-isopropyl-2-oxazlin-2-yl)pyridine]VCl$_3$

[2,6-Bis-(4S-isopropyl-2-oxazlin-2-yl)pyridine] (0.266 g, 0.88 mmole) and VCl$_3$(3THF) (0.300 g, 0.80 mmole) were dissolved in 40 mL of THF. The slurry was stirred for 20 hours resulting in the formation of a purple solid. The product was isolated by filtration, washing with Et2O, and drying under vacuum (0.335 g, 91.0 percent yield).

17. Preparation of [2,6-Bis-(4S-isopropyl-2-oxazlin-2-yl)pyridine]TiCl$_3$

[2,6-Bis-(4S-isopropyl-2-oxazlin-2-yl)pyridine] (0.268 g, 0.89 mmole) and TiCl$_3$(3THF) (0.300 g, 0.81 mmole) were dissolved in 40 mL of THF. The slurry was stirred for 20 hours resulting in the formation of a blue solid. The product was isolated by filtration, washing with Et$_2$O, and drying under vacuum (0.320 g, 86.7 percent yield).

18. Preparation of [2,6-Bis-(4S-isopropyl-2-oxazlin-2-yl)pyridine]ScCl$_3$

[2,6-Bis-(4S-isopropyl-2-oxazlin-2-yl)pyridine] (0.329 g, 0.109 mmole) and ScCl$_3$ (0.15 g, 0.99 mmole) were dissolved in 30 mL of THF. The slurry was stirred for 20 hours resulting in the formation of a white solid. The product was isolated by filtration, washing with Et$_2$O, and drying under vacuum (0.395 g, 88.0 percent yield).

Example 19

Preparation of [2,6-Bis-(2-benzimidazolyl)pyridine)FeCl$_2$

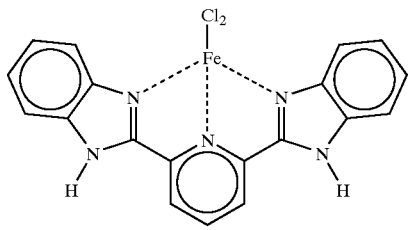

2,6-Bis-(2-benzimidazolyl)pyridine (0.540 g, 1.74 mmole) and FeCl2 (0.200 g, 1.58 mmole) were dissolved in 30 mL of THF, The slurry was stirred for 20 hours resulting in the formation of blue solids. The microcrystalline product was isolated by filtration, washing with THF, and drying under vacuum (0.61 g, 88 percent yield).

Polymerizations

A stirred 1-liter Parr reactor was used in the polymerizations. All feeds were passed through columns of alumina and a decontaminant (Q-5® catalyst available from Englehardt Chemicals Inc.) prior to introduction into the reactor. Catalyst and cocatalysts are handled in a glovebox containing an atmosphere of argon or nitrogen. The reactor is charged with about 240 g of mixed alkanes solvent (isopar E™, available from Exxon Chemicals Inc.) and 300 g of propylene and heated to the reaction temperature of 70° C. Methylalumoxane is combined with the metal complex in toluene solution at a molar ratio of 1000:1 and allowed to stand at 25° C. for 15 minutes prior to use. The catalyst composition is transferred to a catalyst addition tank, and injected into the reactor. The polymerization conditions are maintained for 15 minutes. The resulting solution is removed from the reactor, and 10 ml of a toluene solution containing approximately 67 mg of a hindered phenol antioxidant (Irganox™ 1010 from Ciba Geigy Corporation) and 133 mg of a phosphorus stabilizer (Irgafos™ 168 from Ciba Geigy Corporation) are then added.

Polymers are recovered by drying the recovered reaction mixture in a vacuum oven set at 140° C. for about 20 hours. Polymerization results are contained in Table 1.

TABLE 1

| Run | catalyst | Efficiency (g polymer/mg metal) | Tacticity (percent mm) | Mw/Mn |
|---|---|---|---|---|
| 1 | Ex. 5 | 41.6 | 97.8 | 196,000/78,700 = 2.48 |
| 2 | Ex. 12 | 6.4 | — | 155,000/42,700 = 3.61 |
| 3 | Ex. 14 | 22.0 | 91.5 | 190,000/50,900 = 3.72 |
| 4 | Ex. 16 | 6.9 | — | — |
| 5 | Ex. 19 | 14.0 | 96.8 | 131,000/47,000 = 2.79 |
| 6 | CrCl$_2$ | 6.4 | — | — |

What is claimed is:

1. A process for polymerizing olefins comprising contacting ethylene, one or more C$_{3-20}$ α-olefins, or a mixture thereof with a catalyst composition for olefin polymerization comprising:

(A) a metal complex comprising a multidentate chelating ligand, said metal complex corresponding to the formula:

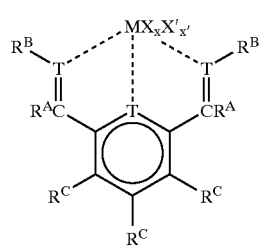

I where M is a metal from one of Groups 3 to 13 of the Periodic Table of the Elements, the lanthanides or actinides;

T is nitrogen or phosphorus;

R$^A$ independently each occurrence is T'R$^B{}_j$,

R$^B$ independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl- substituted hydrocarbyl, and the R$^B$ and R$^A$ groups bonded to the same T═C grouping are joined together to form a divalent ligand group;

j is 1 or 2, and when j is 1, T' is oxygen or sulfur and when j is 2, T' is nitrogen or phosphorus, $R^C$ independently each occurrence is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl- substituted hydrocarbyl, or two $R^C$ groups are joined together forming a divalent ligand group;

X is an anionic ligand group having up to 60 atoms (excluding ligands that are cyclic delocalized π-bound ligand groups), or two X groups together form a divalent anionic ligand group;

X' independently each occurrence is a Lewis base ligand having up to 20 atoms;

x is a number from 0 to 5; and x' is zero, 1 or 2; and (B) an activating cocatalyst wherein the molar ratio of (A) to (B) is from 1:10,000 to 100:1.

2. The process of claim 1, wherein M is a metal of Groups 5–8;

T is nitrogen;

X is chloride or $C_{1-10}$ hydrocarbyl; and x' is zero.

3. The process of claim 2 wherein $R^C$ is hydrogen.

4. The process of claim 1 wherein the metal complex is:

[2,6-Bis-(4S-isopropyl-2-oxazlin-2-yl)pyridine]MnCl$_2$,
[2,6-Bis-(4S-isopropyl-2-oxazlin-2-yl)pyridine]CrCl$_2$,
[2,6-Bis(4S-isopropyl-2-oxazlin-2-yl)pyridine]FeCl$_2$,
[2,6-Bis-(4S-isopropyl-2-oxazlin-2-yl)pyridine]FeCl$_3$,
[2,6-Bis-(4S-isopropyl-2-oxazlin-2-yl)pyridine]TiCl$_3$,
[2,6-Bis-(4S-isopropyl-2-oxazlin-2-yl)pyridine]TiCl$_3$
[2,6-Bis-(4S-isopropyl-2-oxazlin-2-yl)pyridine]ScCl$_3$,
or [2,6-Bis-(2-benzimidazolyl)pyridine]FeCl$_2$.

5. The process of any one of claims 1–4 wherein the activating cocatalyst is a polymeric or oligomeric alumoxane, a mixture of a polymeric or oligomeric alumoxane with one or more $C_{1-20}$ hydrocarbyl substituted Group 13 metal Lewis acid compounds, a mixture of an aliphatic or aromatic ether and a polymeric or oligomeric alumoxane, or a mixture of an aliphatic or aromatic ether, a polymeric or oligomeric alumoxane, and one or more $C_{1-20}$ hydrocarbyl substituted Group 13 metal Lewis acid compounds.

6. The process of claim 1 wherein propylene is polymerized under polymerization conditions to form isotactic polypropylene.

7. The process of claim 1 wherein styrene or a non-conjugated diene is additionally copolymerized.

* * * * *